(12) United States Patent
Rinner

(10) Patent No.: US 8,419,779 B2
(45) Date of Patent: Apr. 16, 2013

(54) SYSTEMATIC DISPLACEMENT BONE SCREW

(76) Inventor: James A. Rinner, Raymond, WI (US)

( * ) Notice: Subject to any disclaimer, the term of this patent is extended or adjusted under 35 U.S.C. 154(b) by 598 days.

(21) Appl. No.: 12/633,277

(22) Filed: Dec. 8, 2009

(65) Prior Publication Data

US 2011/0137355 A1   Jun. 9, 2011

(51) Int. Cl.
*A61B 17/86* (2006.01)
*A61F 2/08* (2006.01)

(52) U.S. Cl.
USPC .......................................................... 606/317

(58) Field of Classification Search ............... 606/301, 606/307, 309, 312, 315, 317, 318; 411/307–311, 411/411, 413, 424
See application file for complete search history.

(56) References Cited

U.S. PATENT DOCUMENTS

| | | |
|---|---|---|
| 341,146 A | 5/1886 | Howes |
| 1,451,484 A | 4/1923 | Woodward |
| 1,980,093 A | 11/1934 | Rosenberg |
| 2,301,181 A | 11/1942 | Ilsemann |
| 2,371,365 A | 3/1945 | Tomalis et al. |
| 2,636,194 A | 4/1953 | Schneider |
| 2,788,046 A | 4/1957 | Rosan |
| 3,186,464 A | 6/1965 | Baumle |
| 3,412,773 A | 11/1968 | Breed |
| 3,426,642 A | 2/1969 | Phipard, Jr. |
| 3,466,748 A | 9/1969 | Christensen |
| 3,530,920 A | 9/1970 | Podell |
| 3,701,372 A | 10/1972 | Breed |
| 3,972,360 A | 8/1976 | Cadwallader |
| 4,059,102 A | 11/1977 | Devas |
| 4,175,555 A | 11/1979 | Herbert |
| 4,258,607 A | 3/1981 | McKewan |
| 5,120,171 A | 6/1992 | Lasner |
| 5,147,363 A | 9/1992 | Harle |
| 5,180,382 A | 1/1993 | Frigg et al. |
| 5,226,766 A | 7/1993 | Lasner |
| 5,259,398 A | 11/1993 | Vrespa |
| 5,417,533 A | 5/1995 | Lasner |
| 5,456,685 A | 10/1995 | Huebner |
| 5,562,672 A | 10/1996 | Huebner et al. |
| 6,572,315 B1 * | 6/2003 | Reed .............................. 411/307 |
| 8,128,671 B2 * | 3/2012 | Taylor ........................... 606/315 |
| 2005/0147943 A1 | 7/2005 | Chang |
| 2007/0053765 A1 | 3/2007 | Warnick et al. |

* cited by examiner

*Primary Examiner* — Anu Ramana

(57) ABSTRACT

The present invention is a systematic displacement bone screw having minor and major thread diameters that are constant instead of tapered. The crests at the tip of the screw are narrower than the crests near the screw head resulting in a smaller distance between the thread flanks, which displaces and/or compresses more bone matter. Because the major diameter remains constant, the diameter of the hole made by inserting the screw is consistent over the length of the screw allowing the screw to be adjusted without loosening. The systematic displacement screw with varying crest thicknesses also avoids the need to use a larger diameter screw in place of a removed screw during a repair procedure. Rather than increasing the size of the hole, the systematic displacement screw can be used for the both the original screw and the replacement screw.

6 Claims, 5 Drawing Sheets

SYSTEMATIC DISPLACEMENT BONE SCREW

CROSS-REFERENCE TO RELATED APPLICATIONS

None

FIELD OF INVENTION

The present invention relates to the field of bone screws used during orthopedic surgery.

GLOSSARY

Figure 1:
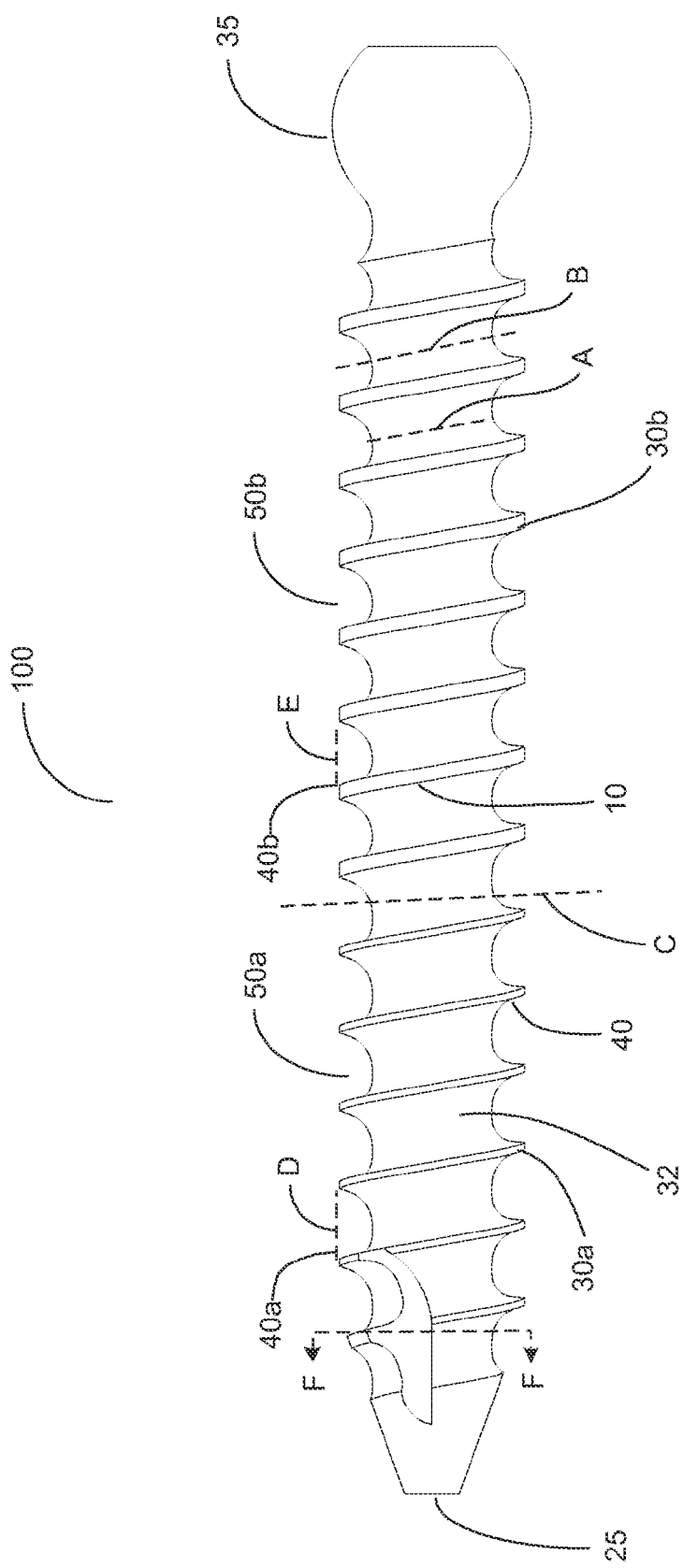
FIG. 1 illustrates a side view of an exemplary embodiment of a systematic displacement bone screw.

As used herein, the term "screw" refers to a structure adapted to receive a torque force, and is comprised of a screw body having a minor diameter surrounded by a helical crest structure having a major diameter, a head and a distal end located opposite to the screw head.

As used herein, the term "screw head" refers to the portion of the screw to which torque is applied.

As used herein, the term "thread" refers to the helical protruding portion of a screw which engages or displaces surrounding material (e.g., bone) with which the screw comes in contact.

As used herein, the term "taper" or "tapered" refers to an elongated structure with a gradual diminution of width or thickness.

As used herein, the term "crest" refers to the portion of a screw which is farthest from the body of the screw and which is defined by the flanks of the thread.

As used herein, the term "flank" refers to the vertical protuberance which extends between the crest and the root of a screw.

As used herein, the term "flank spacing" refers to the distance between flanks.

As used herein, the term "progressive flank spacing" refers to a pattern where the distance between the flanks successively increases or decreases from one end of the screw to the other.

As used herein, the term "root" refers to the narrow inner surface between the threads of a screw.

As used herein, the term "major diameter" refers to the diameter at the crest of a screw.

As used herein, the term "minor diameter" refers to the diameter at the root of a screw.

As used herein, the term "bone screw" or "orthopedic screw" refers to an implant inserted into a bone to immobilize or stabilize fractured bone segments or as part of a surgical construct.

As used herein, the term "cannula" refers to a tubular shaped opening in a bone screw for inserting a guide pin or wire.

As used herein, the term "lateral cut" refers to a portion removed from a screw to form teeth for easier insertion of a bone screw into a bone.

As used herein, the term "bone aperture" refers to an opening in a bone made by the insertion of a bone screw.

As used herein, the term "constant aperture" refers to an opening in a bone that does not increase in width as a screw is progressively inserted.

As used herein, the term "pedicle" refers to a bone which supports the upper structure of the vertebrate.

As used herein, the term "surgical construct" refers to a system or subsystem of interactive components which stabilize a bone structure. A surgical construct may include, but is not limited to constructs used to fuse bones, connect bones, separate bones, reposition bones, attach ligaments or any other function which is used to correct related medical conditions.

BACKGROUND

Orthopedic surgeons often use bone screws as a component of a stabilizing construct in a bone. Typically, the head of the bone screw will have a recessed socket into which a driver tool is inserted to screw the bone screw into or out of a patient's bone. There is often a need to adjust the insertion depth of the bone screw so that the head of the bone screw is at a desired height/position above the bone.

A conventional orthopedic bone screw has either a straight major and minor diameter or a combination of straight and tapered major and minor diameters. The flank spacing, major diameter and minor diameter may vary between types of orthopedic screws.

When a conventional orthopedic screw is inserted into a bone, bone is displaced. One problem with a conventional tapered orthopedic bone screw is that it is narrowest at the insertion point and tapers to a larger diameter at the head. As the screw is inserted into the bone, the tapered thread displaces more bone along its axis as the screw is driven into place. This results in a snug fit as long as the screw remains in its initial position. If the screw is reversed, which causes the screw thread to back out, there is a gap between the screw form and the prior displaced bone, resulting in an instable construct.

A further related problem known in the art is that during subsequent orthopedic surgeries, known in the art as revision or repair surgeries, a bone screw often must be removed (e.g., as a result of loosening) and replaced with a larger screw. Because it is a general practice to initially use the largest diameter screw possible, a larger diameter screw cannot be used to the replace the initial screw. Removing the initial screw without a replacement results in a less structurally sound construct.

Bone loss due to successive insertion of orthopedic screws is undesirable, particularly with respect to osteoporotic bone, i.e., bones that are weakened by a decrease in bone density making them more susceptible to fractures.

Bone screws known in the prior art typically have minor and major diameters that are tapered so that the diameter increases from the tip of the screw to the head which increasingly compresses the bone as the bone screw is screwed deeper into the bone, resulting in a tight fit. These bone screws are tapered not only to provide an increasing compressive fit as the screw is screwed into the bone, but also to increase the loading force on the screw near the screw head. The thicker screw portion near the head makes the screw strongest where the lateral load on the screw is the greatest. An example of a tapered bone screw is disclosed by U.S. Pat. No. 5,226,766 (Lasner '766).

Tapered bone screws, such as the one disclosed by Lasner '766, however, are not desirable. Bone screws are available in various lengths and diameters. For stability and maximum anchoring ability, an orthopedic surgeon will use the largest possible diameter bone screw, i.e., the largest bone screw that will not breech the pedicle wall. During revision/repair surgery, a larger diameter screw may be used to provide secure retention of the repair bone screw in a hole previously used by a then-removed bone screw. If the larger diameter screw causes the pedicle wall to be breeched, the patient may suffer nerve damage. A tapered bone screw also exerts a radial force on the bone which may cause the bone to fracture.

In addition, if a tapered bone screw is ever backed out of the bone for adjustment or replacement of the screw, the replaced bone screw becomes loosened and will not be securely held by the bone due to the mating of the tapered bone screw with the tapered bore in the bone.

It is desirable to have an orthopedic screw which minimizes bones loss and the potential for fracturing, particularity for osteoporotic bone.

It is desirable to have an orthopedic screw which does not create instability during repositioning of the screw, if necessary, as repositioning often results in the creation of a larger hole to screw ratio.

SUMMARY OF THE INVENTION

The present invention is a systematic displacement bone screw having minor and major thread diameters that are constant instead of tapered. The crests at the tip of the screw are narrower than the crests near the screw head resulting in a smaller distance between the thread flanks, which displaces and/or compresses more bone matter. Because the major diameter remains constant, the diameter of the hole made by inserting the screw is consistent over the length of the screw allowing the screw to be adjusted without loosening. In addition, the screw does not exert a radial force that could split the bone.

The systematic displacement bone screw with varying crest thicknesses also avoids the need to use a larger diameter screw in place of a removed screw during a repair procedure. Rather than increasing the size of the hole, the systematic displacement screw can be used for the both the original screw and the replacement screw. If a tapered screw is initially used, a systematic displacement bone screw having a major diameter that is identical to the screw being removed can be used as a replacement screw during a repair surgery.

The systematic bone screw is also ideal for osteoporotic bone because the smaller distances between the flanks could increase the density of the diseased bone.

DETAILED DESCRIPTION OF INVENTION

For the purpose of promoting an understanding of the present invention, references are made in the text to exemplary embodiments of a systematic displacement bone screw, only some of which are described herein. It should be understood that no limitations on the scope of the invention are intended by describing these exemplary embodiments. One of ordinary skill in the art will readily appreciate that alternate but functionally equivalent dimensions and designs may be used. The inclusion of additional elements may be deemed readily apparent and obvious to one of ordinary skill in the art.

Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

FIG. 1 illustrates a side view of an exemplary embodiment of systematic displacement bone screw 100. Systematic displacement bone screw 100 is comprised of root 32 having thread 10. In the embodiment shown, thread 10 has a constant pitch.

In the embodiment shown, minor diameter 15 (represented by line A) and major diameter 20 (represented by line B) of systematic displacement bone screw 100 remain constant the length of the screw while the thickness of crest 30 varies. A constant minor diameter 15 and a constant major diameter 20 allow the screw to be adjusted without loosening.

In the exemplary embodiment shown, systematic displacement bone screw 100 has a minor diameter of 4.2 mm and a major diameter of 6.5 mm, but may be of any dimensions known in the art.

In the embodiment shown, systematic displacement bone screw 100 includes threaded regions 50a, 50b (separation designated by line C). Region 50a is proximate to tip 25 and has crests 30a which are thinner than crests 30b of region 50b, which is proximate to head 35. Various embodiments may include more or fewer threaded regions. The widths of the crests are constant within each region. In the embodiment shown, crests 30a have a width of approximately 0.25 mm and crests 30b a width of approximately 0.5 mm. In other embodiments, the number of crests in each region and the width of the crests vary.

A constant minor diameter 15 and a constant major diameter 20 result in similarly dimensioned flanks 40. Flank 40 extends from root 32 to crest 30. However, the distance between flanks 40 varies depending on the width of crests 30. In the embodiment shown, flank spacing 40a is represented as the distance between two crests in region 50a (line D). Flank spacing 40b is represented as the distance between two crests in region 50b (line E). In the embodiment shown, flank spacing 40a is greater than flank spacing 40b. That is, as the width of the crests increases, the flank spacing decreases to account for the additional width.

In the embodiment shown, crests 30 are flat; however, in other embodiments, crests may be angled, pointed, rounded or of another shape or contour known in the art.

Figure 2:
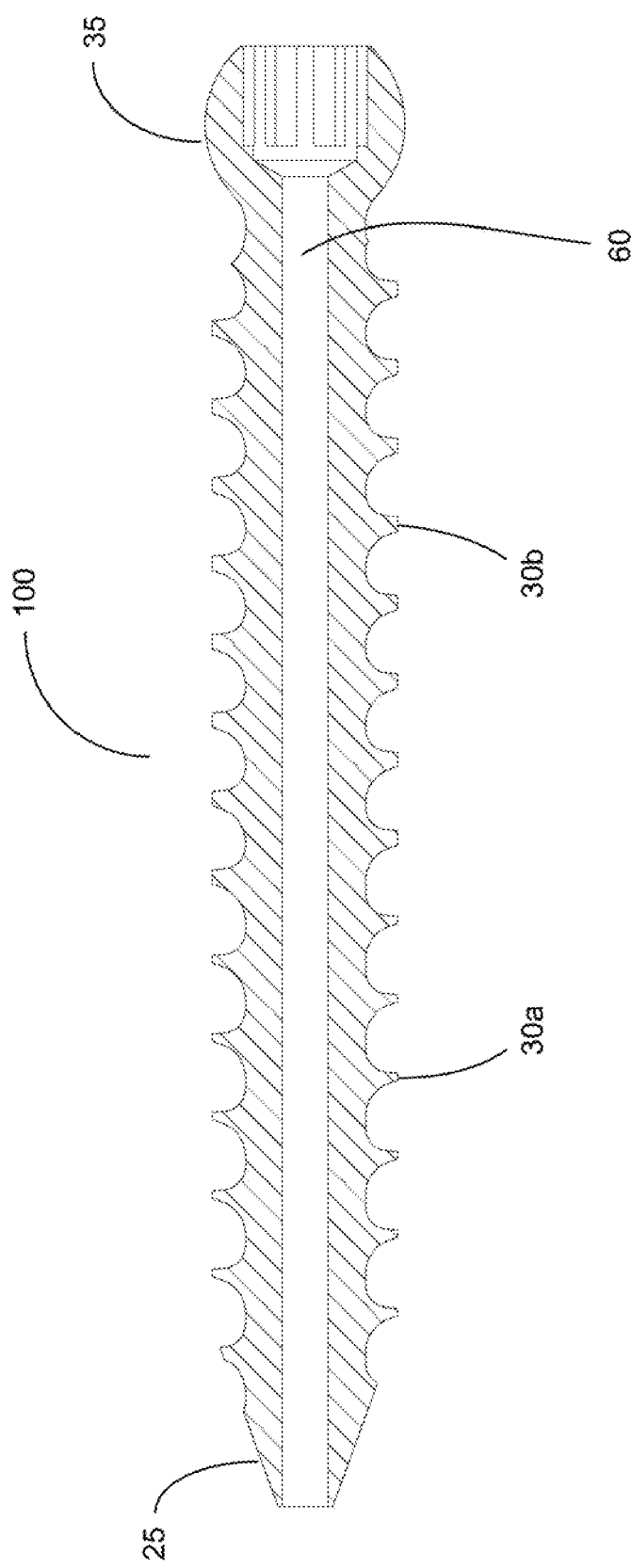
FIG. 2 illustrates a cross sectional view of an exemplary embodiment of a systematic displacement bone screw.

FIG. 2 illustrates a cross sectional view of exemplary embodiment of a systematic displacement bone screw 100.

In the embodiment shown, bone screw 100 further includes cannula 60 which may be inserted onto and passed along a trocar wire into a pre-drilled hole in a bone during insertion of bone screw 100. In other embodiments, bone screw 100 is solid, i.e., does not include a cannula.

Figure 3:
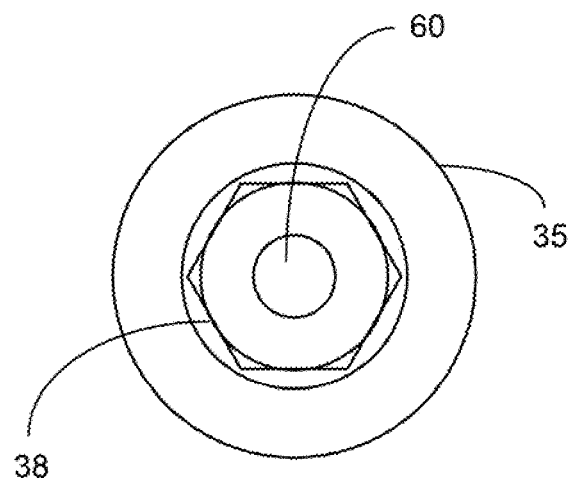
FIG. 3 illustrates an end view of the proximal end of an exemplary embodiment of a systematic displacement bone screw.

FIG. 3 illustrates an end view of the proximal end of an exemplary embodiment of systematic displacement bone screw 100. Visible are screw head 35, socket 38 and cannula 60. In the embodiment shown, screw head is circular and socket is hexagonal. In other embodiments, screw heard and socket may be square, octagonal, or of any other shape which could be used with orthopedic surgery instruments.

Figure 4:
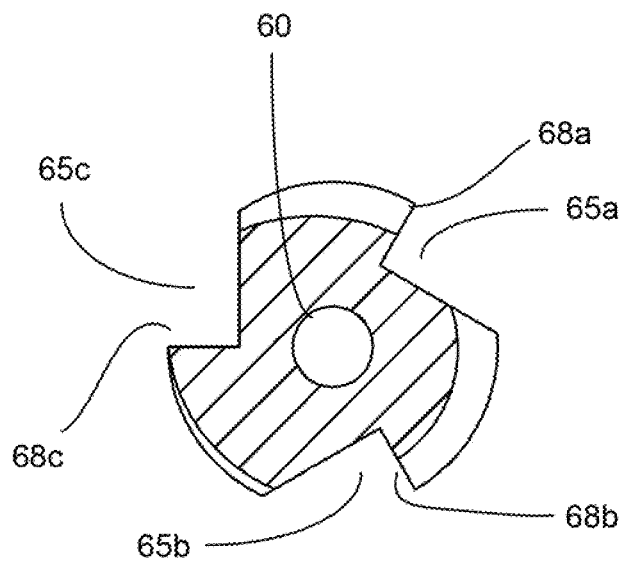
FIG. 4 illustrates a cross sectional view of the distal end of an exemplary embodiment of a systematic displacement bone screw.

FIG. 4 illustrates a cross sectional view of the distal end of an exemplary embodiment of systematic displacement bone screw 100 taken along line F-F shown in FIG. 1. In the embodiment shown, tip 25 is tapered at an angle and has three equally spaced lateral cuts 65a, 65b, 65c which form teeth 68a, 68b, 68c to facilitate insertion of bone screw 100 into the bone. In other embodiments, tip 25 may have more or fewer lateral cuts and teeth which may be equally or unequally spaced or no lateral cuts at all.

Figure 5:
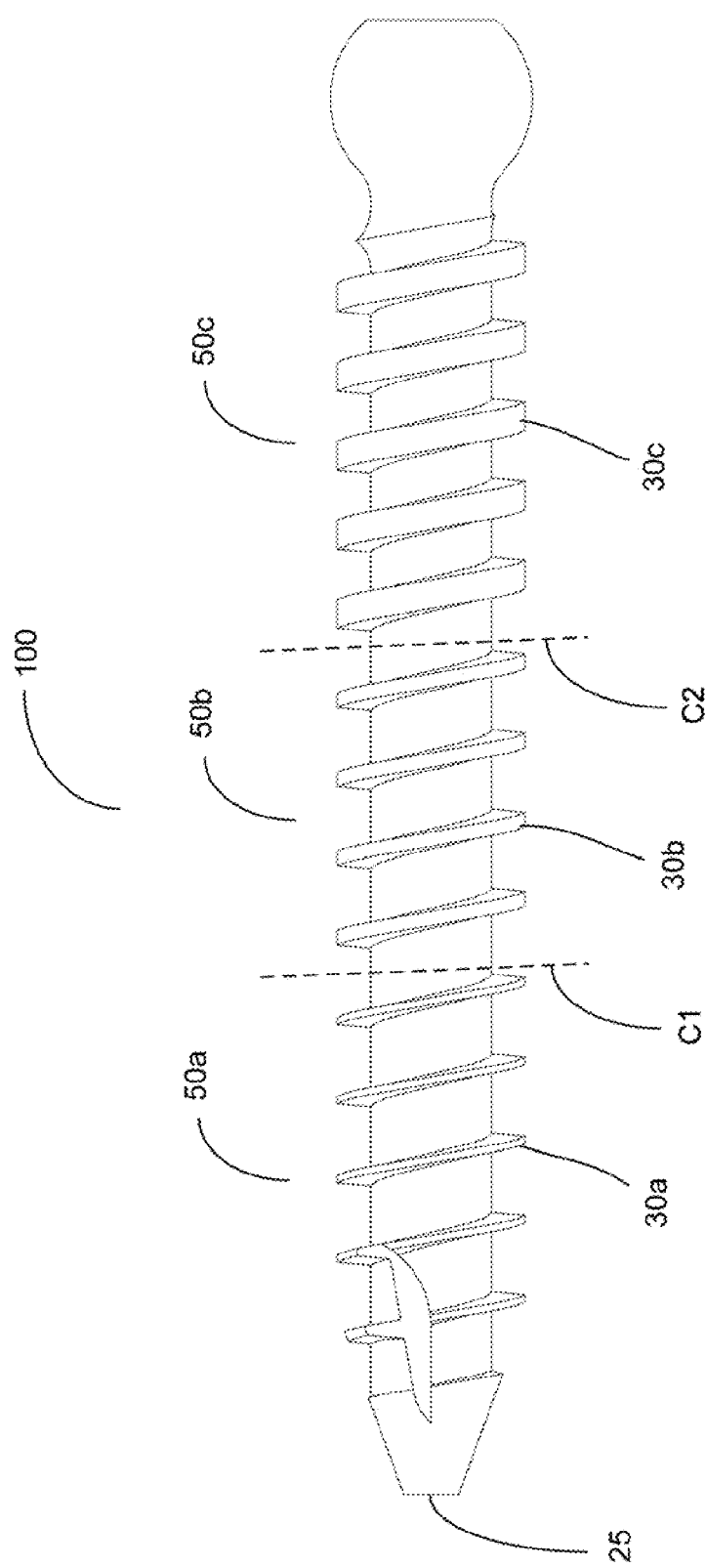
FIG. 5 illustrates a side view of a second exemplary embodiment of a systematic displacement bone screw.

FIG. 5 illustrates a side view of a second exemplary embodiment of systematic displacement bone screw 100. In the embodiment shown, systematic displacement bone screw 100 has three different threaded regions 50a, 50b, 50c (separation designated by lines C1 and C2). Region 50a is proximate to tip 25 and has crests 30a which are thinner than crests 30b of region 50b, and crests 30c of region 50c which is proximate to head 35. The widths of the crests are constant within each region. In the embodiment shown, crests 30a have a width of approximately 0.25 mm and crests 30b a width of approximately 0.5 mm, and crests 30c a width of approximately 0.75 mm. In other embodiments, the number of crests in each region and the width of the crests vary.

Figure 6:
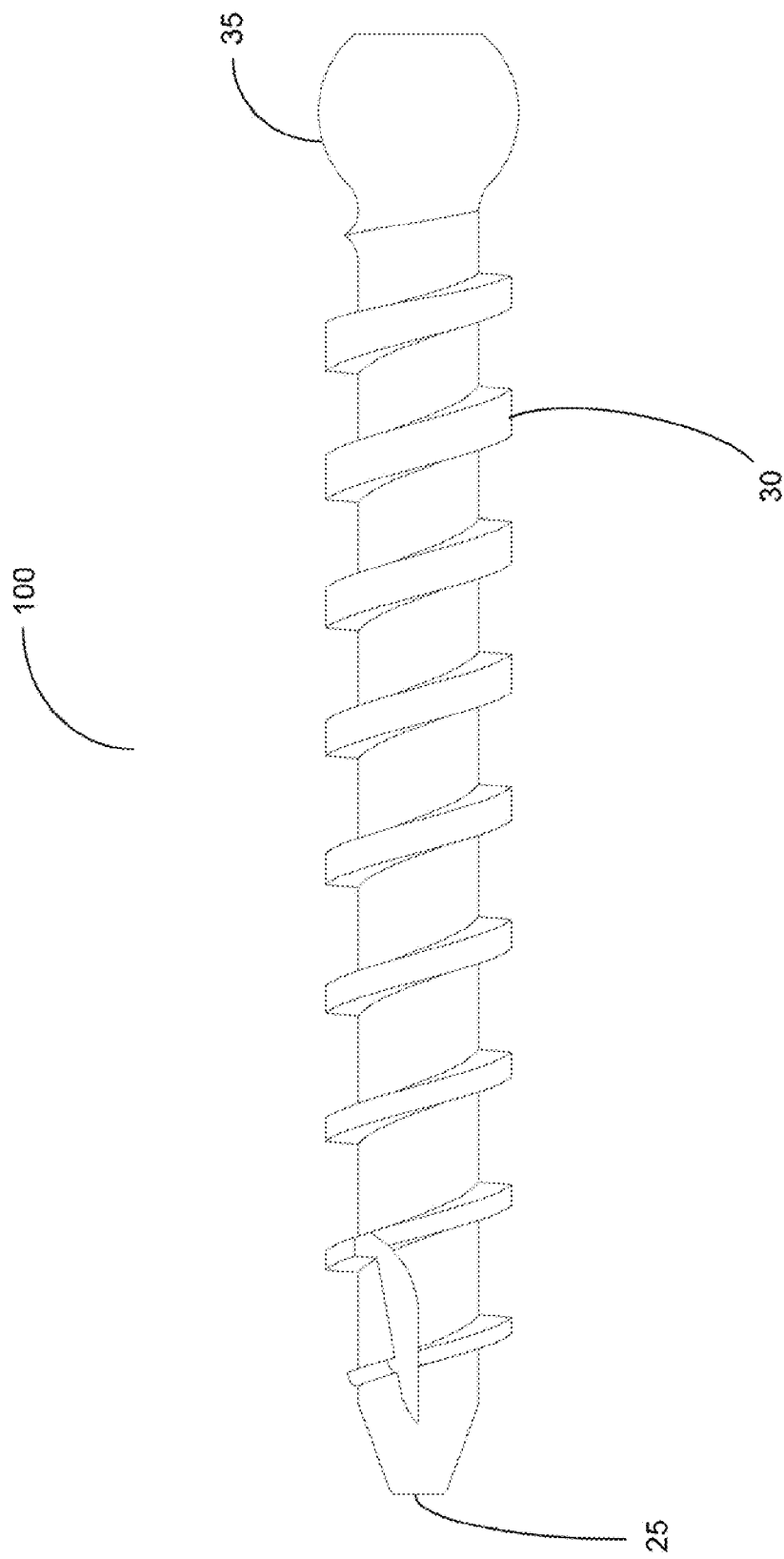
FIG. 6 illustrates a side view of a third exemplary embodiment of a systematic displacement bone screw.

FIG. 6 illustrates a side view of a third exemplary embodiment of systematic displacement bone screw 100. In the embodiment shown, the width of crests 30 increases successively over the length of bone screw 100 with the narrowest crest located at tip 25 and the widest crest at the head 35.

In another embodiment, a plurality of systematic displacement bone screws 100 are provided in a kit. Bone screws 100 would have constant minor and major diameters, but would vary in the widths of the crests. For example, a kit may includes screws with two threaded regions with varying crest widths, screws with three threaded regions of varying crest widths and screws with crest widths that successively increase.

Using the kit of bone screws 100, an orthopedic surgeon may remove a bone screw from a bone, select a screw from the kit having a wider crest than the crest width of the screw being removed and replaced, and then replace the removed screw with the selected screw from the kit. The wider crest width of the selected screw will provide a secure anchoring of the selected screw in the bone without increasing the major diameter of the screw being used.

Systematic displacement bone screw 100 is manufactured using a cylindrical blank material having a head, tip and a diameter consistent with the desired major diameter of the finished bone screw. A tool for cutting thread known in the art is positioned and the blank material is advanced toward the cutting tool. The blank is rotated cutting a helical path along the blank creating the thread. The rate of lateral movement of blank material determines the pitch and crest width. For bone screws having a constant crest width, only one cutting pass is needed.

To create a bone screw with more than one crest width, i.e., a screw with more than one threaded regions, additional cutting passes are required. The cutting tool is repositioned back to the origin of its cutting pass and is then shifted from that origin a distance to a new position. The shift represents the desired difference in crest widths between the narrower (first) crest width and the wider (second) crest width. The process is repeated for each subsequent threaded region.

The rotational speed at which the screw is turned and the rate of advancement of the screw with respect to the tool remains the same as in the first cutting pass causing the tool to trace a shifted helical path producing both thick and thin crest widths for a thread of the same pitch for both threaded regions.

The same tool is then used to smoothly blend the step discontinuity in the transition region between the two threaded regions.

What is claimed is:

1. A systematic displacement bone screw for maximizing bone displacement through a bone aperture which remains constant in size, comprising:
   a root;
   a plurality of bone compressing flanks extending outwardly from said root, each flank having a crest width;
   each flank separated from an adjacent flank by a flank spacing;
   a screw tip;
   a screw head;
   a major diameter that is constant along the length of the screw;
   a minor diameter that is constant along the length of the screw;
   wherein the crest width of each flank progressively increases from said screw tip to said screw head such that a flank with the smallest crest width is adjacent to said screw tip and a flank with the largest crest width is adjacent to said screw head; and
   wherein the flank spacing between adjacent flanks progressively decreases from said screw tip to said screw head.

2. The systematic displacement bone screw of claim 1 wherein a crest of one or more of said flanks is flattened.

3. The systematic displacement bone screw of claim 1 wherein a crest of one or more of said flanks is rounded.

4. The systematic displacement bone screw of claim 1 wherein at least one crest of said flank is rounded and at least one crest of said flanks is flattened.

5. The systematic displacement bone screw of claim 1 wherein said tip has at least one lateral cut which forms a tooth.

6. A method of orthopedic revision surgery to replace a first bone screw in a bone aperture of a patient with a replacement bone screw without significantly increasing a diameter of the bone aperture, comprising:
   removing said first bone screw from the bone aperture; and
   replacing said first bone screw with said replacement bone screw;
   wherein said replacement bone screw comprises a root; a plurality of bone compressing flanks extending outwardly from said root, each flank having a crest root width; each flank separated from an adjacent flank by a flank spacing; a screw tip; a screw head; a major diameter that is constant along the length of the replacement bone screw; and a minor diameter that is constant along the length of the replacement bone screw; wherein the crest width of each progressively increases from said screw tip to said screw head such that a flank with the smallest crest width is adjacent to said screw tip and a flank with the largest crest width is adjacent to said screw head; and wherein the flank spacing between adjacent flanks progressively decreases from said screw tip to said screw head.

* * * * *